US012138056B2

(12) United States Patent
Valent et al.

(10) Patent No.: US 12,138,056 B2
(45) Date of Patent: Nov. 12, 2024

(54) METHODS AND SYSTEMS FOR OBTAINING AN ELECTROCARDIOGRAM SIGNAL OF A PATIENT VIA A NON-ADHERING, DIRECT CONTACT ELECTRODE APPARATUS

(71) Applicant: GE Precision Healthcare LLC, Wauwatosa, WI (US)

(72) Inventors: Thomas Valent, Burlington, WI (US); Nancy Stoffel, Schenectady, NY (US); Mohammad Mohammad Khair, Whitefish Bay, WI (US); Steven Falk, Baltimore, MD (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 18/335,901

(22) Filed: Jun. 15, 2023

(65) Prior Publication Data
US 2023/0320644 A1    Oct. 12, 2023

Related U.S. Application Data

(63) Continuation of application No. 16/411,022, filed on May 13, 2019, now Pat. No. 11,717,207, which is a
(Continued)

(51) Int. Cl.
*A61B 5/24*    (2021.01)
*A61B 5/00*    (2006.01)
*A61B 5/25*    (2021.01)

(52) U.S. Cl.
CPC .............. *A61B 5/25* (2021.01); *A61B 5/6846* (2013.01); *A61B 5/0006* (2013.01); *A61B 2503/045* (2013.01)

(58) Field of Classification Search
CPC ........... A61B 5/25; A61B 5/26; A61B 5/6846; A61B 5/0006; A61B 2503/045;
(Continued)

(56) References Cited

U.S. PATENT DOCUMENTS

| 3,888,240 A | 6/1975 | Reinhold, Jr. et al. |
| 7,245,956 B2 | 7/2007 | Matthews et al. |

(Continued)

FOREIGN PATENT DOCUMENTS

| DE | 202006007226 U1 | 9/2007 |
| EP | 2659832 A1 | 11/2013 |
| WO | 2018004614 A1 | 1/2018 |

OTHER PUBLICATIONS

ISA European Patent Office, International Search Report Issued in Application No. PCT/US2020/020924, Aug. 6, 2020, WIPO, 6 pages.
(Continued)

*Primary Examiner* — Adam Z Minchella
(74) *Attorney, Agent, or Firm* — McCoy Russell LLP

(57) ABSTRACT

Various methods and systems are provided for a fabric cover including a plurality of integrated electrodes for measuring an electrocardiogram signal of a patient in direct contact with at least a subset of the plurality of integrate electrodes. As one example, a fabric cover for an infant incubator or warmer includes a plurality of electrodes spaced apart from one another within a measurement area of a surface of the fabric cover adapted to have direct contact with a patient, the plurality of electrodes including a topmost electrode extending across an entire width of the measurement area, a bottommost electrode extending across the entire width of the measurement area, and a set of electrodes arranged between the topmost electrode and bottommost electrode, in a direction perpendicular to the width, within the measurement area.

17 Claims, 9 Drawing Sheets

Related U.S. Application Data continuation-in-part of application No. 16/294,711, filed on Mar. 6, 2019.

(58) Field of Classification Search
CPC ........... A61B 5/28; A61B 5/304; A61B 5/308; A61B 5/318; A61B 5/363
See application file for complete search history.

(56) References Cited

U.S. PATENT DOCUMENTS

| | | |
|---|---|---|
| 2004/0111045 A1 | 6/2004 | Sullivan et al. |
| 2006/0224089 A1* | 10/2006 | Tan ................... A61B 5/4806 600/595 |
| 2011/0288605 A1* | 11/2011 | Kaib ................. A61B 5/14542 607/5 |
| 2012/0323132 A1* | 12/2012 | Warner ................. G16H 40/63 600/509 |
| 2014/0100436 A1 | 4/2014 | Brunner et al. |
| 2017/0303810 A1* | 10/2017 | Stone ................... A61B 5/6893 |
| 2018/0296118 A1 | 10/2018 | Bishay et al. |
| 2018/0360324 A1 | 12/2018 | Lorraine et al. |
| 2019/0059752 A1* | 2/2019 | Botsva .................. A61B 5/332 |

OTHER PUBLICATIONS

ISA European Patent Office, Written Opinion of the International Searching Authority Issued in Application No. PCT/US2020/020924, Aug. 6, 2020, WIPO, 10 pages.

* cited by examiner

METHODS AND SYSTEMS FOR OBTAINING AN ELECTROCARDIOGRAM SIGNAL OF A PATIENT VIA A NON-ADHERING, DIRECT CONTACT ELECTRODE APPARATUS

CROSS-REFERENCE TO RELATED APPLICATIONS

The present application is a continuation of U.S. patent application Ser. No. 16/411,022, filed May 13, 2019, which is a continuation-in-part of U.S. patent application Ser. No. 16/294,711, filed Mar. 6, 2019. The entire contents of each of the above applications are hereby incorporated by reference for all purposes.

FIELD

Embodiments of the subject matter disclosed herein relate to an apparatus including a plurality of electrodes, the apparatus adapted to have direct, but non-adhering, contact with and measure an electrocardiogram signal of a patient.

BACKGROUND

An electrocardiogram (ECG) may provide a measurement of electric signals of the heart. Standard methods for measuring electric potential (e.g., bio-potentials) of a patient, and obtaining an ECG signal of the patient, may include securing electrodes directly to the skin of a patient. For example, a plurality of electrodes may be adhered to the patient's skin via an adhesive. An acquired ECG signal may be used to diagnose heart conditions of the patient, as well as determine a heart rate of the patient. The heart rate may be used for patient monitoring and diagnosis. When used in neonatal or infant care applications (often directly following delivery of the neonate/infant), the ECG signal and/or heart rate may be needed during resuscitation and/or monitoring of the patient for additional interventions.

BRIEF DESCRIPTION

In one embodiment, a fabric cover for an infant incubator or warmer includes: a plurality of electrodes spaced apart from one another within a measurement area of a surface of the fabric cover adapted to have direct contact with a patient, the plurality of electrodes including a topmost electrode extending across an entire width of the measurement area, a bottommost electrode extending across the entire width of the measurement area, and a set of electrodes arranged between the topmost electrode and bottommost electrode, in a direction perpendicular to the width, within the measurement area.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
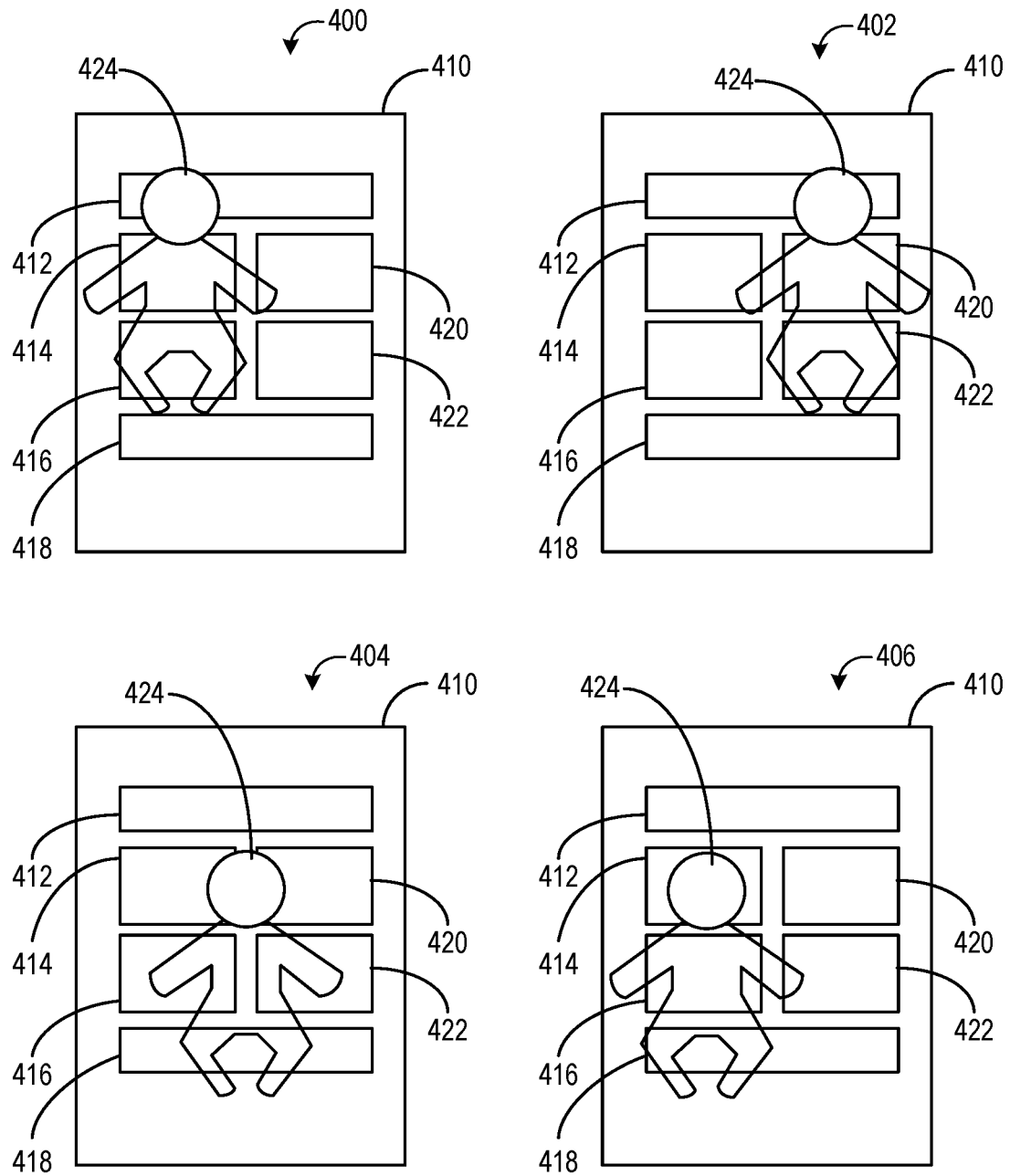
FIG. 4 shows a schematic of example positions of a patient on a fabric cover including a plurality of integrated sensors for measuring bio-potentials of the patient.
Figure 5:
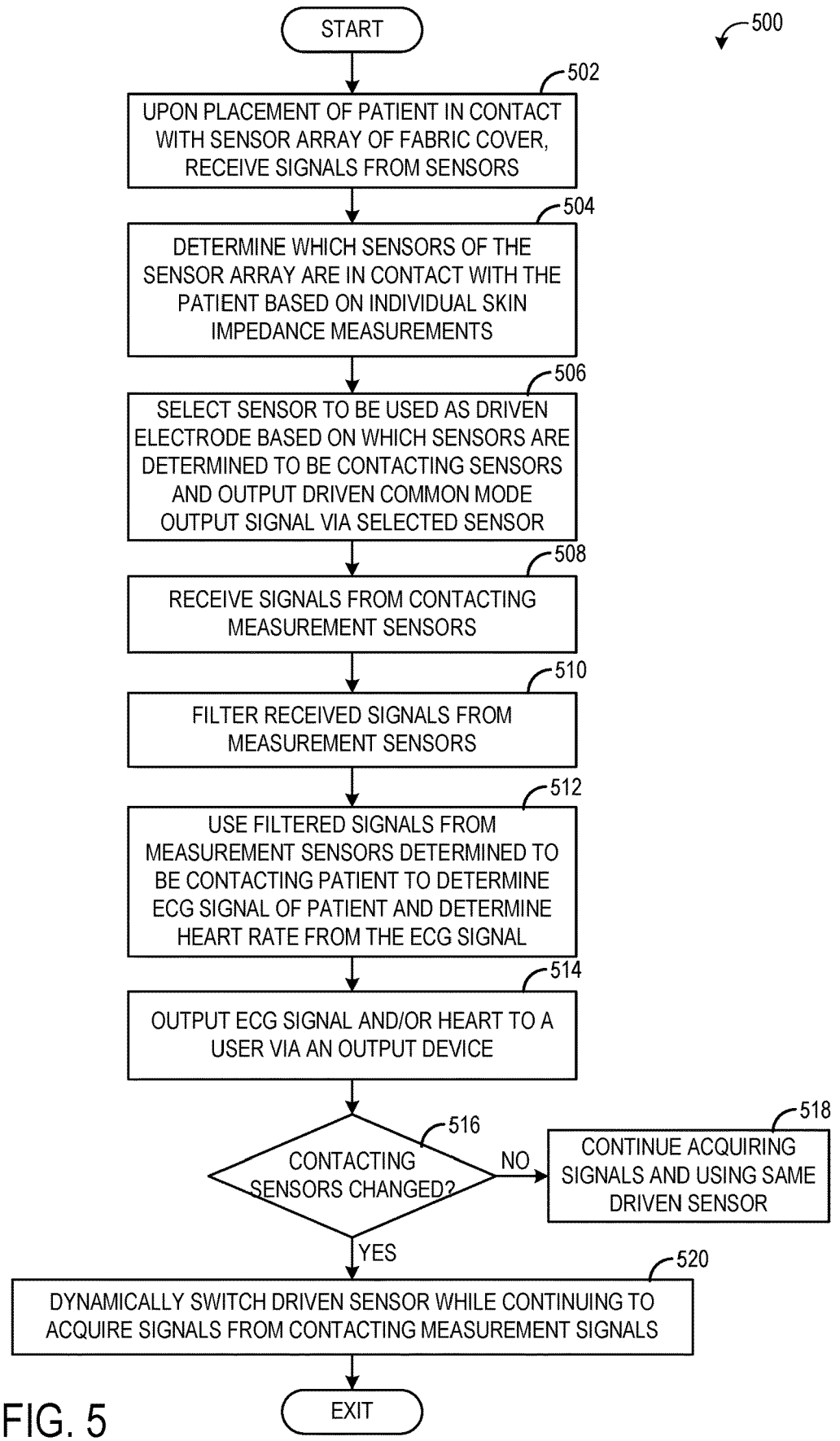
FIG. 5 shows a flow chart of a method for dynamically switching a driven electrode of a sensor array of an apparatus in direct contact with a patient and determining an electrocardiogram (ECG) signal and/or heart rate of the patient from signals acquired from a plurality of measurement electrodes of the sensor array.

The following description relates to various embodiments of an apparatus (e.g., fabric cover) including a plurality of electrodes for measuring an electrocardiogram signal of a patient in direct contact with at least a subset of the plurality of electrodes. For monitoring and care of a patient, such as a neonate or infant, an electrocardiogram (ECG) and/or heart rate signal of the patient may be acquired and displayed to a user (e.g., medical professional). As introduced above, standard electrodes for measuring an ECG signal of a patient may be adhered to the skin of the patient. However, such electrodes which are stuck to the patient's skin may cause damage to the more delicate skin of neonates or infants. Further, it may take a while for a medical professional to attach all the ECG leads (e.g., electrodes). However, the time to attach the ECG electrodes is often critical for administering essential and life-saving care to the neonate or infant. In one example, after birth, a neonate or infant may be placed in neonate or infant care environment (which may include a bassinet, warmer or incubator), on top of a platform or mattress. An apparatus, such as a fabric cover (which may be in the form of a blanket, bed sheet, or mattress cover in some embodiments) may include a plurality of electrodes (also referred to herein as sensors) attached or integrated therein. The fabric cover including an arrangement of electrodes may then be positioned in direct contact with the patient (e.g., placed on top of the mattress, with the patient lying directly on the fabric cover). When the patient is placed on the fabric cover with electrodes embedded therein, for example, a signal processing circuit, such as the signal processing circuit shown in FIGS. 2 and 3, of or in electronic communication with electrodes of the fabric cover may automatically and immediately start acquiring bio-potential signals of the patient. Though the electrodes of the fabric cover may be in direct contact with the skin of the patient, they may not be physically adhered (e.g., stuck) to the patient. As a result, as shown in FIG. 4, the patient may be able to move around across a surface of the electrodes and fabric cover, thereby changing which electrodes of the fabric cover are in direct contact with the skin of the patient. The electrodes may be arranged in an array and include a plurality of measurement electrodes (adapted to measure bio-potentials of the patient) and one or more dedicated, driven electrodes (adapted to output a driven, common mode output signal adapted to reduce noise of the measured bio-potential signals). The acquired bio-potential signals may then be used to determine an ECG signal and/or heart rate of the patient. As shown by the method of FIG. 5, which of the electrodes are being used as the driven electrode for data acquisition may be dynamically switched during operation, based on which electrodes are determined to be in direct contact with the patient. As a result, a more accurate ECG signal with reduced noise may be obtained (continuously, in one example), even while a patient moves around on top of or against the fabric cover. This system may have minimal, passive contact with the patient, while still allowing for direct contact with the skin of the patient. As a result, an impact to the infant/neonate may be reduced.

Figure 1:
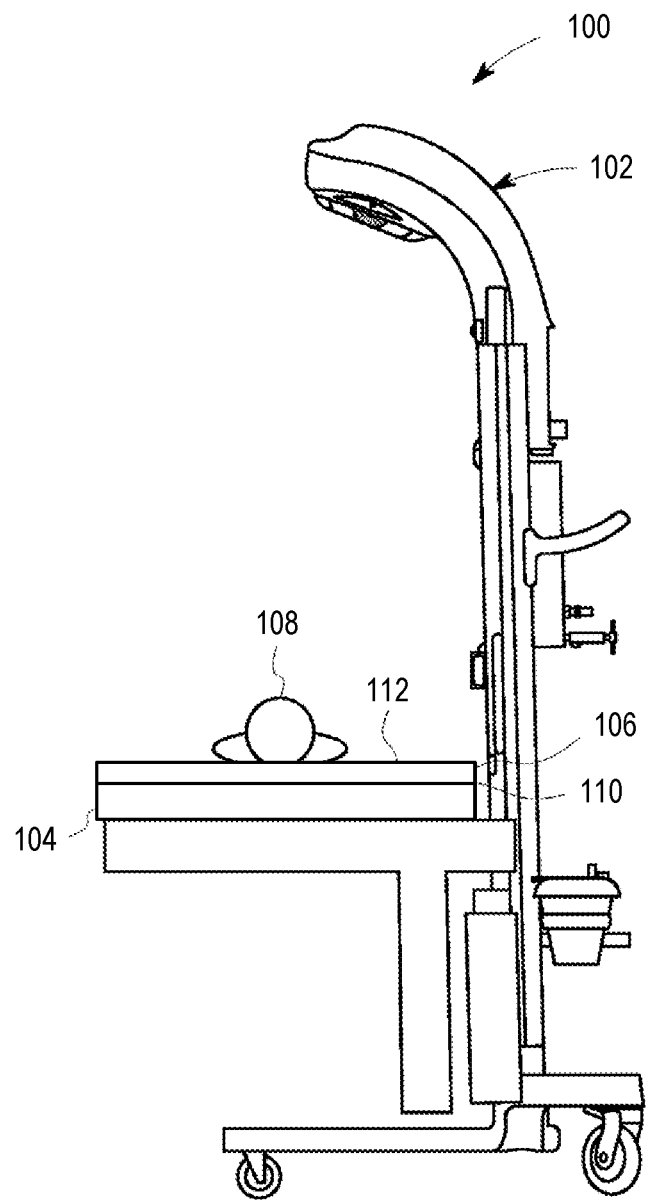
FIG. 1 shows an example of a neonate or infant care environment including a fabric cover with integrated sensors for direct contact with a patient.

FIG. 1 shows an example of a neonate or infant care environment including a fabric cover with incorporated (e.g., integrated in one embodiment) sensors for direct contact with a patient. Specifically, FIG. 1 shows a neonatal or infant care environment 100. As shown in FIG. 1, environment 100 may include a neonate/infant radiant warmer 102, which may be referred to as a baby warmer that may include a mattress 104 for supporting a patient 108 (e.g., a neonate or infant). In alternate embodiments, environment 100 may be an incubator. In alternate embodiments, environment 100 may be a bassinet. The incubator and/or warmer and/or bassinet may be used in the neonatal intensive care unit (NICU) and/or right after labor and delivery of an infant.

An apparatus 110 having a sensor array is positioned between the mattress 104 and the patient 108. As used herein, the sensor array and sensors may also be referred to as an electrode array and electrodes, respectively. In the example shown in FIG. 1, the apparatus 110 is a fabric cover 106 that is positioned on/over the mattress 104 such that a top surface 112 of the fabric cover 106 is in direct contact with the patient 108. The fabric cover 106 includes a plurality of electrodes (e.g., sensors) integrated therein for measuring bio-potentials of the patient 108. As described further below, the plurality of electrodes may be arranged on the top surface 112 such that they may have direct contact with the skin of the patient 108. In one example, the fabric cover 106 may be a type of mattress pad or bed sheet. In another example, the fabric cover 106 may be a blanket.

Figure 11:
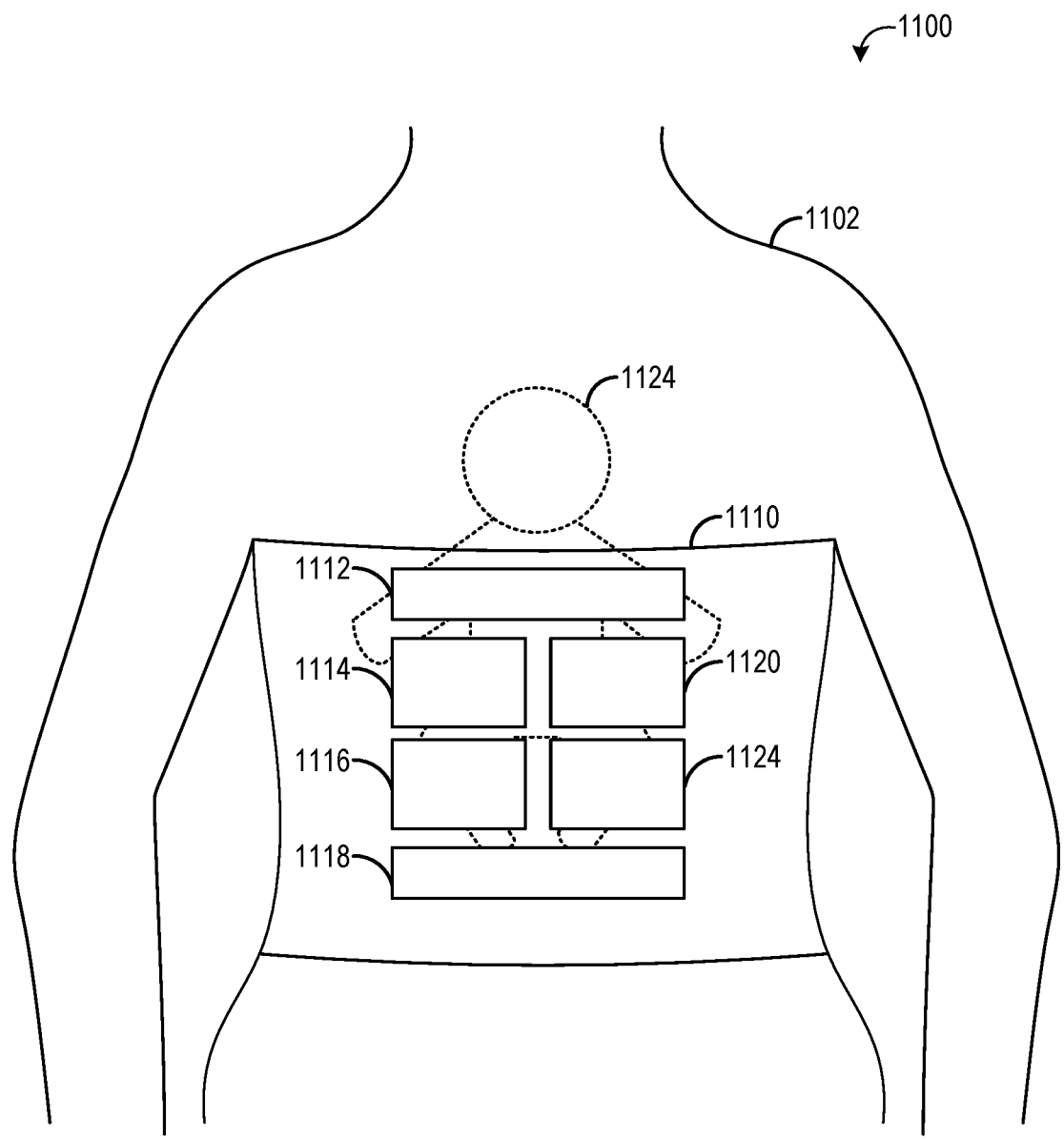
FIG. 11 shows a schematic view of a fabric cover configured to facilitate skin-to-skin contact between a patient and a care provider while measuring bio-potentials of the patient.

As described further herein, the apparatus 110 may provide electrocardiogram (ECG) monitoring of patients such as neonates or infants. Apparatus 110 may consist of multiple sensors (e.g., electrodes) defining an array of sensors integrated with a remainder of the apparatus 110 (e.g., integrated with or sewn into a fabric of the fabric cover 106). The apparatus 110 may be transportable and reusable (e.g., washable). Further, the apparatus 110 may be inserted under the patient, such as a neonate or infant, and upon any surface, such as a blanket, mattress (as shown in FIG. 1), or mother's chest or abdomen (as shown in FIG. 11). For example, as shown in FIG. 11 and as described further below, the apparatus 110 may be integrated into a kangaroo care/wearable, skin-to-skin application, such as a sling, halter, wrap, nursing top, and the like. As described further below, apparatus 110 may include electronics for direct contact measurement of bio-potentials (e.g., heart rate), signal conditioning and processing, and/or wired or wireless communication with additional electronics, processors, or control units. Apparatus 110 may be configured for rapid measurement of ECG signals, even in the case where there is movement of the patient across the surface of the apparatus 110 (such that the patient changes which sensors/electrodes of the apparatus 110 are in direct contact with the patient). For example, apparatus 110 may enable measurement of ECG signals through motion artifacts associated with the patient's movements on the apparatus 110 (e.g., on the bed sheet or blanket).

Figure 2:
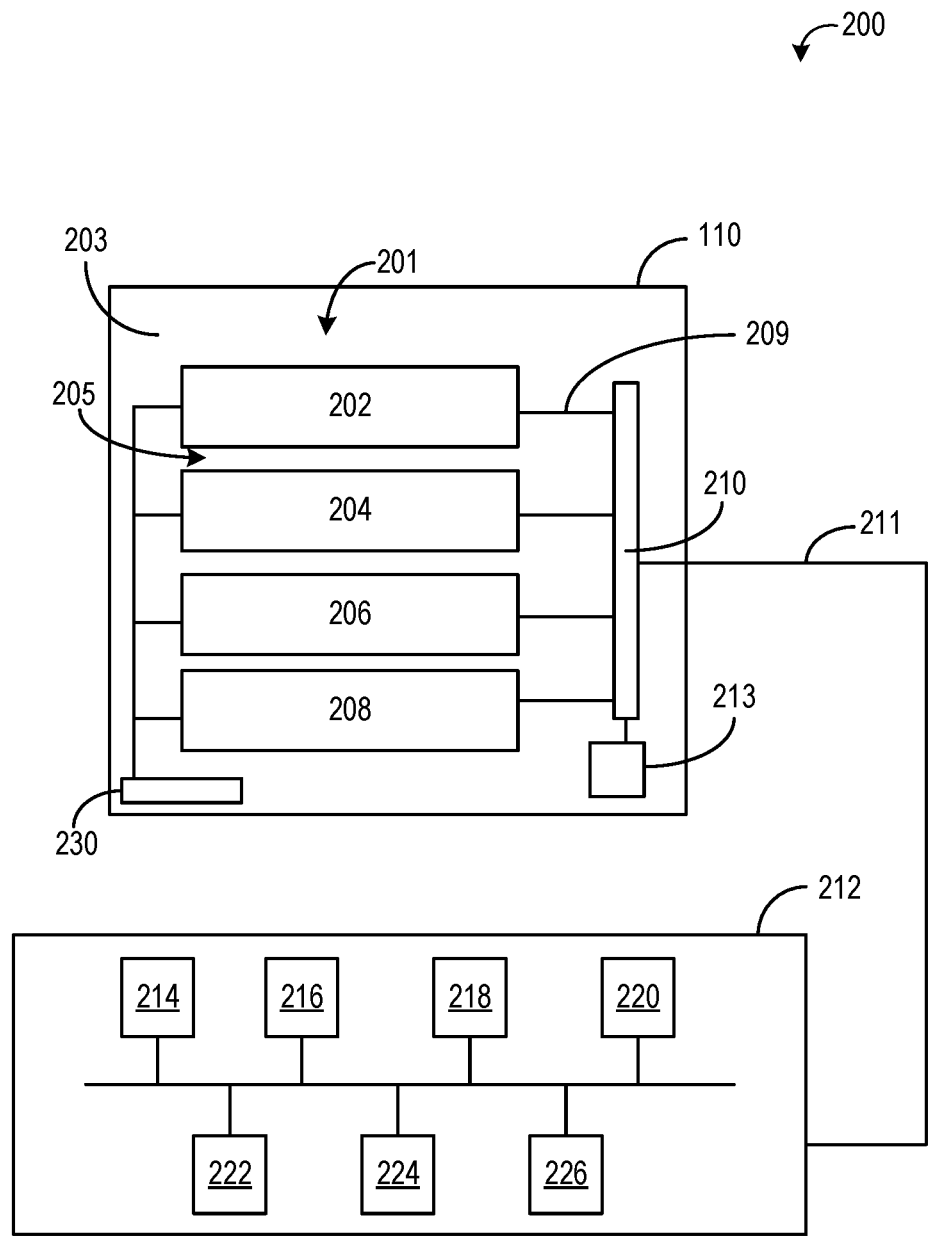
FIG. 2 shows an example block diagram of a system for measuring bio-potentials of a patient including an apparatus having a sensor array and a signal processing circuit.

FIG. 2 shows an example block diagram of a system 200 for measuring bio-potentials of a patient (e.g., neonate or infant) including an apparatus 110 having a sensor array 201 and a signal processing circuit 212. The apparatus 110 may be a fabric cover (such as fabric cover 106 shown in FIG. 1, which may be a bed sheet, mattress cover, and/or blanket, in some embodiments, or such as fabric cover 1110 of FIG. 11, which may be a halter, sling, wrap, or the like). Thus, apparatus 110 may be or include a fabric base 203 with a plurality of individual sensors or electrodes (202, 204, 206, and 208) of the sensor array 201 integrated (e.g., embedded, sewn, incorporated, or affixed in some way) therein. As shown in FIG. 2, sensor array 201 includes four individual sensors 202, 204, 206, and 208, all spaced apart from one another (e.g., not touching or directly contacting one another) via a gap (e.g., distance) 205. However, in alternate embodiments, sensor array 201 may include more or less than four individual sensors (e.g., two, three, five, eight, ten, etc.). The individual sensors of sensor array 201 may be arranged in a pattern. Examples of different patterns of sensors of the sensor array for apparatus 110 are shown in FIGS. 4 and 6-10. For all patterns, the individual sensors may be spaced apart from one another so that an amount of fabric of the fabric base 203 electrically insulates adjacent sensors from one another. In this way, electrical signals are not transferred between sensors.

In one embodiment, each of the sensors of sensor array 201 may be an electrode adapted to measure bio-potentials of the patient in direct contact with a surface of the sensors. The sensors (e.g., sensors 202, 204, 206, and 208) may also be referred to herein as ECG sensors since they are adapted to measure electrocardiogram (ECG) signals from the patient and determine a heart rate of the patient based on the measured signals. Sensor array 201 may include a plurality of measurement electrodes (e.g., which receive and measure ECG signals from the patient) and one or more dedicated, driven electrodes (e.g., which output a driven common mode output signal to the patient). In some examples, each of the measurement electrodes may be switched to be a driven electrode (e.g., switched from receiving bio-potential signals from the patient to delivering the common mode output signal to the patient). However, all of the dedicated, driven electrodes may remain driven electrodes and may not be switchable to measurement electrodes. In this way, the electrodes designated as dedicated, driven electrodes may only be used to output the driven common mode output signal and may not be used for measuring bio-potentials of the patient. As described further below, at any one time, one or multiple sensors may be selected to actively be the driven electrode and deliver the driven, common mode output signal. In one embodiment, first sensor 202, second sensor 204, and third sensor 206 may be measurement electrodes while fourth sensor 208 is a dedicated, driven electrode. In another embodiment, first sensor 202 and second sensor 204 may be measurement electrodes while third sensor 206 and fourth sensor 208 are dedicated, driven electrodes. In yet another embodiment, each of first sensor 202, second sensor 204, third sensor 206, and fourth sensor 208 may be measurement sensors adapted to be individually switched to functioning as a driven electrode. In yet another embodiment, each of first sensor 202, second sensor 204, third sensor 206, and fourth sensor 208 may be measurement sensors and where second sensor 204 and third sensor 206 are adapted to be both switched to functioning as a driven electrode. In this way, different combinations of measurement and driven electrodes included in sensor array 201 are possible.

Each individual sensor (202, 204, 206, and 208) is electrically coupled to an electronic connector 210 via a different electrical connection 209. In one embodiment, the electrical connections 209 may be conductive threads woven or imbedded within the fabric base 203. In this way, electrical signals may be passed back and forth between the individual sensors and the connector 210. For example, signals received by measurement electrodes from the patient may be transferred to the connector 210 via corresponding electrical connections 209 and the driven common mode output signal may be sent to the driven electrode from the connector 210 via corresponding electrical connection 209. A single connector 210 is shown in FIG. 2. However, in alternate embodiments, there may be multiple connectors (e.g., one for each individual sensor of sensor array 201).

The signal processing circuit 212 of system 200 is electrically coupled to the connector 210 (or connectors) via a wired or wireless connection 211. In one embodiment, all or select parts of the signal processing circuit 212 may be included within apparatus 110 and the processed signals may be transferred via a wireless connection to additional processing electronics or a remote data acquisition and/or display device. In this embodiment, the connector(s) 210 may be omitted. Alternatively or additionally, the apparatus 110 may include an integrated electronic layer 213 electrically coupled to (and/or included within) the connector 210 and adapted to perform measurements on electrical signals received from the plurality of sensors. For example, the integrated electronic layer may include one or more components of signal processing circuit 212 and/or dynamic switching circuit 300 (as described further below with reference to FIG. 3). In another embodiment, as shown in FIG. 2, all the components of the signal processing circuit 212 may be located separate (e.g., remote) from the apparatus 110 and thus the connector(s) 210 and wired or wireless connection 211 may transfer electrical signals (acquired measurements and the driven signal) between the apparatus 110 and the signal processing circuit 212. In some embodiments, the connector 210 may include a wireless pod including a transmitter/receiver for transferring wireless signals between the apparatus 110 and the signal processing circuit 212. In another embodiment, apparatus 110 may include a separate wireless pod electrically coupled with the connector 210 or each individual sensor of sensor array 201. In still another embodiment, such as when the sensors and/or connector 210 are wirelessly connected to the signal processing circuit 212, the sensors may receive electrical power via a battery 230 incorporated into the apparatus 110 (e.g., incorporated into the fabric cover).

In one embodiment, signal processing circuit 212 may be processor based. In one embodiment, signal processing circuit 212 may include one or more input/output interface devices 214 for communication with, e.g., sensors 202, 204, 206, and 208 of sensor array 201, and/or one or more external processing circuits. One or more input/output interface devices 214 may include associated analog to digital and or digital to analog circuitry for facilitating bi-directional signal communication with sensor array 201. Signal processing circuit 212 may also include one or more central processing units (CPU) 216, one or more memory devices 218 (e.g. a random access memory (RAM) and/or cache memory, which may be volatile), one or more storage devices (e.g., non-volatile storage devices) 220, and one or more output devices 222. One or more memory devices 218 and/or one or more storage devices 220 may define a tangible computer readable storage medium of signal processing circuit 212. Signal processing circuit 212 may also include a power supply 224 which may be a battery-based power supply to facilitate mobile operation of signal processing circuit 212. One or more output devices 222, in one embodiment, may be provided, e.g., by one or more of a display with or without an associated touch screen and/or one or more audio output devices (e.g., a speaker). Devices 214, 216, 218, 220, 222, and 224, in one embodiment, are in communication via a system bus 226. Signal processing circuit 212 may output data via an output device 222 which may include a bus-connected output device, as shown in FIG. 2 and/or to an output device of apparatus 110 which is provided as an output device in communication with signal processing circuit 212 via input/output interface device 214.

Figure 3:
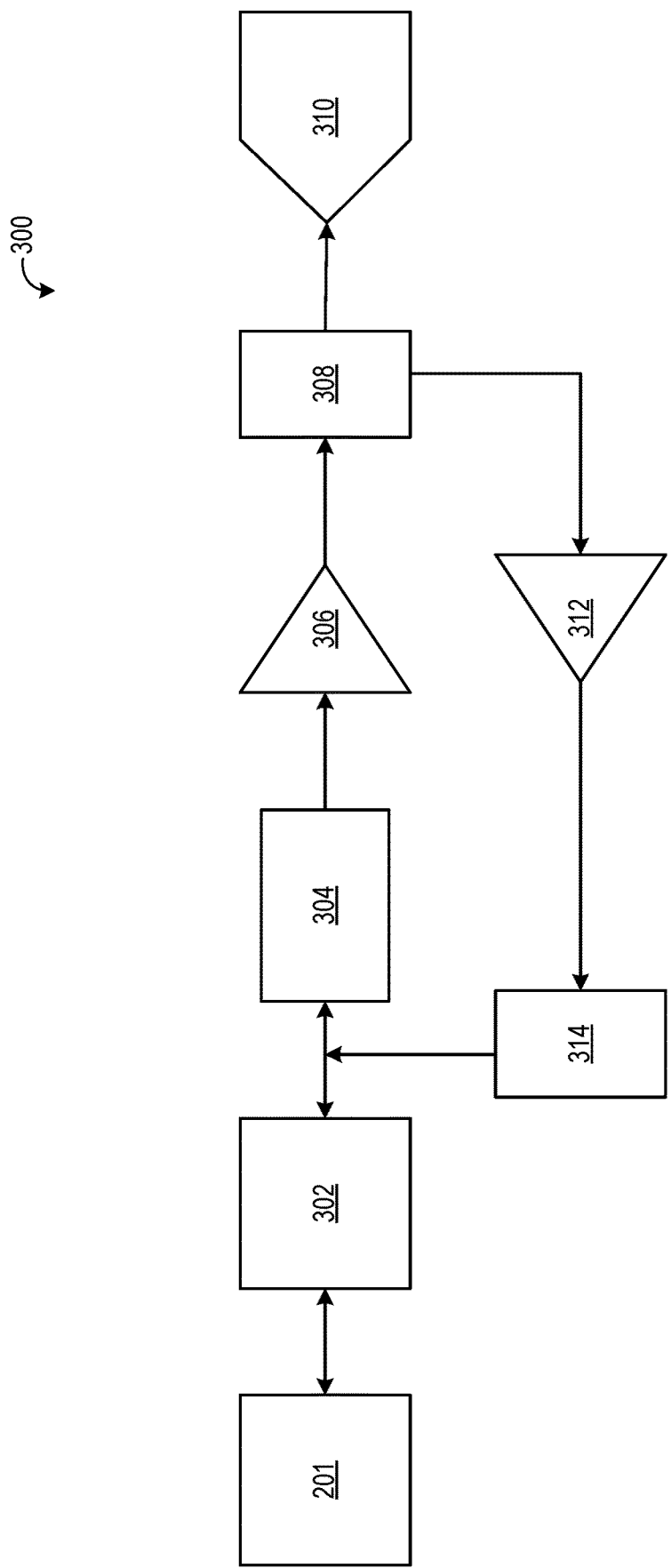
FIG. 3 shows an example of a dynamic switching circuit for controlling the sensors of the sensor array of FIG. 2.

FIG. 3 shows an example of a dynamic switching circuit 300 for controlling the ECG sensors (e.g., sensors 202, 204, 206, and 208) of the apparatus 110. In one embodiment, the dynamic switching circuit 300 may be part of the signal processing circuit 212, such as part of the CPU 216. In another embodiment, the dynamic switching circuit 300 may be included on/within the apparatus 110, such as part of and/or electrically connected with connector 210 (e.g., via integrated electronic layer 213).

Dynamic switching circuit 300 includes sensor array 201 which includes a plurality of ECG sensors (e.g., electrodes). As discussed above with reference to sensor array 201 and FIG. 2, at least one (and in some examples, at least two) of the ECG sensors of sensor array 201 are dedicated, driven electrodes which selectively output a driven common mode output signal and a plurality of the ECG sensors are measurement electrodes adapted to measure bio-potentials of the patient and output these signals for determining the ECG signal of the patient. The measurement electrodes may also be switched to selectively output the driven common mode output signal. Further, as described below, more than one of the switchable measurement electrodes may be selected at any one time to output the driven common mode signal. However, the dynamic switching circuit 300 may dynamically switch which one of the available electrodes outputs the driven common mode signal, based on which sensors have direct contact with skin of the patient lying on the apparatus 110.

Looking at FIG. 3, dynamic switching circuit 300 includes ECG sensors of sensor array 201 in two-way electronic communication with defibrillator protection circuitry 302. The defibrillator protection circuitry 302 may include a plurality of resistors and/or additional circuitry elements that absorb repetitive defibrillation and other high-energy pulses (such as electrostatic discharge) to protect more sensitive electronic circuitry elements in the dynamic switching circuit 300 and/or apparatus 110. The defibrillator protection circuitry 302 is electrically coupled, via two-way electronic communication, to one or more input filters 304. As one example, the one or more input filters 304 may include one or more filters (e.g., band-pass filters, adaptive filters, or the like) that filter out noise (such as common motion/movement noise from the patient moving over/across the ECG electrodes) in the signals measured by the measurement electrodes (and which are used to determine the ECG signal of the patient). If using one or more adaptive filters to filter out common motion noise, at least two input channels, each including at least 2 contact points between the ECG sensors and the patient's skin, and one driving electrode may be required. For example, in this case, at least two of the ECG sensors in sensor array 201 which are determined to be in direct contact with the patient's skin (e.g., at least a threshold portion of the sensor is in direct contact with the patient, as explained further below) may be selected as measurement electrodes and a different (third) one of the ECG sensors in sensor array 201, which is also determined to be in direct contact with the patient's skin, may be selected as the driving electrode. The adaptive filter may adjust the frequency range of signals received from the patient and may be executed by CPU 216.

Filtered signals from the input filter(s) 304 are electrically transferred to one or more ECG differential amplifiers 306 for amplifying the measured signals from the patient. The amplified signals are then electrically transferred to an input switch matrix 308. In one example, the input switch matrix 308 may determine which of the measurement electrodes of the ECG sensors have contact with the patient's skin and select signals received from those contacting measurement electrodes to transfer to an analog-to-digital converter (ADC) 310 for further processing and determination of the patient's ECG signal and/or heart rate. In this way, the input switch matrix 308 may selectively switch which measurement electrodes are used for obtaining signals used to determine the patient's ECG signal and/or heart rate. Determining which ECG sensors have contact with the patient's skin may include receiving signals from each and every one of the ECG sensors, which may include a measurement of skin impedance of the skin of the patient, and determining which of the ECG sensors has contact with the patient's skin based on which of the skin impedance measurements meet a threshold level (thereby indicating the sensor providing that signal has a threshold amount of contact with the patient's skin and therefore may provide a strong enough signal for measuring the ECG signal of the patient). The signals from the ECG sensors determined to have contact with the patient's skin, and thus which are measurement electrodes, are transferred to ADC 310 for further processing and determination of the patient's ECG signal and heart rate. The measurement electrodes may each be connected to the ADC 310, and the input switch matrix 308 may determine which measurement electrodes have contact with the patient and can thus be used to provide the driven common mode signal back to the patient.

The ADC 310 converts the analog signals, filtered and amplified, from the selected measurement electrodes (ECG sensors) to digital signals for further processing and output. For example, from ADC 310, the converted digital signals may be processed via additional electronics of the signal processing circuit 212 to determine an ECG signal of the patient and a corresponding heart rate of the patient. These determined ECG signals and/or heart rate may then be output to the user via one or more output devices (e.g., output devices 222 of FIG. 2). As one example, the output device may be an electronic display device.

Based on the determination of which ECG sensors have sufficient contact with the patient's skin providing low electrical impedance, and thus are deemed contacting sensors, the input switch matrix 308 may also select which of the measurement electrodes of the ECG sensors should be used as the driven electrode for delivering the driven common mode output signal. For example, the input switch matrix 308 may determine which input measurement electrodes will be used to feed amplifier 312. At least one input measurement electrode may be selected by the input switch matrix 308, for example. In another example, all of the input measurement electrodes may be used to feed amplifier 312, or any subset thereof.

The input switch matrix 308 then communicates the selected ECG sensors to be the driven electrode signal source and deliver those signal sources to a driven common mode output amplifier 312 which may generate the driven common mode output signal. The driven common mode output signal and the selection of the driven electrode is then communicated electronically to an output switch matrix 314. The output switch matrix 314 functions to switch which ECG contact is delivering the driven common mode output signal to the patient and deliver the driven common mode output signal to the selected ECG sensors. In this way, the selection of which measurement electrodes will be switched and used for driven output is determined by the output switch matrix 314.

In this way, signals generated and measured using one or more directly contacting ECG sensors of sensor array 201 may be digitally sampled and combined to form an ECG signal of the patient and determine that patient's heart rate according to the ECG signal. As explained above, the selection of the contacting ECG sensors for determining the ECG signal may include, at the input switch matrix 308, selecting signals from at least two contacting ECG sensors (e.g., two contact points) for measurement signals and selecting one contacting ECG sensor to be the driven electrode. In another example, the input switch matrix 308 may select signals from more than two contacting ECG sensors (if more than two ECG sensors are determined to be contacting the patient) for measurement signals for determining the ECG signal and heart rate of the patient.

Turning now to FIG. 4, a schematic is shown of example positions of a patient 424 on a fabric cover 410. Fabric cover 410 may be similar to apparatus 110 and/or fabric cover 106 discussed above with reference to FIGS. 1-3. As discussed above, the fabric cover 410 includes a plurality of integrated ECG sensors 412, 414, 416, 418, 420, and 422 which may be referred to herein as electrodes or electrode pads. Each of the ECG sensors are spaced apart from one another such that they are electrically insulated from one another (and thus cannot pass signals between one another, thereby reducing signal interference between ECG sensors) via the intervening fabric of the fabric cover 410. FIG. 4 shows an example arrangement of ECG sensors on a surface of the fabric cover 410 which is not meant to be limiting and other arrangements of ECG sensors are possible. As shown in the example of FIG. 4, the ECG sensors include a topmost ECG sensor 412, a top-left ECG sensor 414, a bottom-left ECG sensor 416, a bottommost ECG sensor 418, a bottom-right ECG sensor 422, and a top-right ECG sensor 420. The patient 424 may be smaller than the fabric cover 410 and thus may move around on top of and across the surface of the fabric cover 410. As such, at different points in time, the skin of the patient may be in contact with different ECG sensors of fabric cover 410. Thus, the dynamic switching circuit of the signal processing circuit included in or electrically coupled with the fabric cover 410 (such as dynamic switching circuit 300 of FIG. 3) may switch, in real-time (e.g., dynamically), which ECG sensors are selected as the measurement electrodes and driven electrode for producing the patient's ECG signal and determining the patient's heart rate, based on the patient's position on the fabric cover 410 (as determined according to the methods described herein with reference to FIG. 3 and FIG. 5).

Specifically, FIG. 4 shows a first view 400 of the patient (e.g., neonate or infant) 424 in a first position on the fabric cover 410 (e.g., top-left corner). In this first position, the patient 424 is in contact with the topmost ECG sensor 412, the top-left ECG sensor 414, and the bottom-left ECG sensor 416. While a small portion of the patient's arm may be contacting top-right sensor 420, there may not be enough skin-to-electrode contact to produce a strong enough skin impedance and measurement signal. Thus, the dynamic switching circuit of the fabric cover 410 may select ECG sensors 412, 414, and 416 as the contacting sensors (e.g., the ECG sensors having direct, face-sharing contact with a portion of the skin of the patient 424). One of the contacting ECG sensors 412, 414, and 416 may be selected to be the driven electrode (sensor) while the remaining two are selected as the measurement electrodes. Signals from the remaining ECG sensors (418, 420, 422), which are determined to be non-contacting ECG sensors, may be discarded (or not acquired) and not used to determine the ECG signal and heart rate of the patient. In one embodiment, ECG sensors 416 and 422 may be dedicated, driven electrodes. Thus, the dynamic switching circuit may automatically select bottom-left ECG sensor 416 to deliver the driven common mode output signal. In alternate embodiments, a different one or more of the ECG sensors of fabric cover 410 may be dedicated, driven electrodes. In yet another embodiment, all of the ECG sensors of fabric cover 410 may be measurement electrodes (e.g., none are dedicated to being driven only) adapted to switch between being measurement and driven electrodes (as determined and selected by the dynamic switching circuit). However, by including some dedicated driven electrodes and some switchable measurement electrodes, an electrode surface area is provided that is always available for common mode noise reduction if all of the measurement electrodes can be used to capture the ECG signal (e.g., because the measurement electrodes have good patient contact), which may improve signal processing outcomes to mitigate motion and noise artifacts using adaptive filtering by the CPU. Further, more ECG channels may improve the adaptive filtering outcomes, while using the measurement electrodes for providing the driven output reduces the number of channels available for signal processing post digitization, and thus it may be desirable to provide the dedicated, driven electrodes so that all possible channels may be available for the ECG signal acquisition.

FIG. 4 also shows a second view 402 of the patient 424 in a second position on the fabric cover 410 (e.g., top-right corner). In one example, the patient 424 may have moved from the first position (in first view 400) to the second position (in second view 402), thereby changing which of the ECG sensors the patient 424 is in direct, physical contact with (and thus changing the contact points of fabric cover 410). In this second position, the patient 424 is in contact with the topmost ECG sensor 412, top-right ECG sensor 420, and bottom-right ECG sensor 422. Thus, patient 424 is no longer contacting ECG sensors 414 and 416 and is newly contacting ECG sensors 420 and 422. Thus, in one example, the dynamic switching circuit may switch the driven electrode to be the bottom-right ECG sensor 422 (from the bottom-left ECG sensor 416 in first view 400), in response to the patient moving positions on the fabric cover 410 and changing which ECG sensors are contacting sensors. Further, the dynamic switching circuit may continue to use the topmost ECG sensors 412 as one measurement electrode and switch to using the top-right ECG sensor 420 (instead of the bottom-right ECG sensor 416, as used in first view 400) as a second measurement electrode.

In a third view 404 of FIG. 4, the patient 424 is in a third position on the fabric cover 410 (e.g., central-bottom region). In one example, the patient 424 may have moved from the second position (in second view 402) to the third position (in third view 404), thereby changing which of the ECG sensors the patient 424 is in direct, physical contact with (and thus changing the contact points of fabric cover 410). In this third position, the patient 424 is in contact with the top-left ECG sensor 414, the bottom-left ECG sensor 416, the bottommost ECG sensor 418, the bottom-right ECG sensor 422, and the top-right ECG sensor 420. Thus, patient 424 is no longer contacting the topmost ECG sensor 412, remains in contact with ECG sensors 420 and 422, and is newly contacting ECG sensors 414, 416, and 418 (as compared to second view 402). Thus, in one example, the dynamic switching circuit may maintain the driven electrode as the bottom-right ECG sensor 422 and not switch the driven electrode to a different ECG sensor. Further, the dynamic switching circuit may continue to use the top-right ECG sensor 420 as one measurement electrode and switch to using the top-left ECG sensor 414 and bottommost ECG sensor 418 as additional measurement electrodes. In the case where the bottom-left ECG sensor 416 is a dedicated, driven electrode, it may be used to apply the driven common mode output signal, in addition to the bottom-right ECG sensor 422 that is currently selected as the driven electrode.

In a fourth view 406 of FIG. 4, the patient 424 is in a fourth position on the fabric cover 410 (e.g., bottom-left). In one example, the patient 424 may have moved from the third position (in third view 404) to the fourth position (in fourth view 406), thereby changing which of the ECG sensors the patient 424 is in direct, physical contact with (and thus changing the contact points of fabric cover 410). In this fourth position, the patient 424 is in contact with the top-left ECG sensor 414, the bottom-left ECG sensor 416, and the bottommost ECG sensor 418. Thus, patient 424 is no longer contacting the top-right ECG sensor 420 and bottom-right ECG sensor 422 (e.g., even though a small portion of patient 424 is shown contacting sensor 422, not enough of the patient's skin is in contact with sensor 422, so the measured skin impedance of this sensor is below the threshold level) and remains in contact with ECG sensors 414, 416, and 418 (as compared to third view 404). Thus, in one example, the dynamic switching circuit may switch the driven electrode to be the bottom-left ECG sensor 416 (from the bottom-right ECG sensor 422). Further, the dynamic switching circuit may continue to use the top-left ECG sensor 414 and bottommost ECG sensor 418 as measurement electrodes.

In all of the views of FIG. 4, at least two contacting ECG sensors are selected as measurement electrodes and a different, one contacting ECG sensor is selected as the driven electrode. As such, the patient's ECG signal may be obtained with reduced noise (e.g., reduced noise from motion of the patient) from the acquired signals. As shown in the example of FIG. 4, the ECG sensors used as measurement electrodes and the driven electrode may be selected based on which sensors are determined to be directly contacting the skin of the patient and dynamically switched as the patient moves across the fabric cover, into different contacting positions, at least under some conditions. For example, the dedicated driven electrodes are fixed per the connection to the signal processing circuit 212 via wired or wireless connection 211. The dedicated driven electrodes are always enabled and driven. If using the impedance measurement it is sensed that the driven electrodes are not in contact with the patient, the system may then select which measurement electrodes are to be used for driving the output signal. Which sensors are selected and used as the driven electrode and measurement (e.g., input)

electrodes may be switched at any time during operation of the fabric cover (e.g., while the patient is on and/or in contact with the fabric cover). For example, switching of measurement and driven electrodes may be performed prior to the initial acquisition of the ECG signal (from the measurement electrodes). In another embodiment, switching of the measurement and driven electrodes may occur during ECG acquisition (e.g., while measurement signals are being acquired from the measurement electrodes), in response to determining the contacting ECG sensors have changed (e.g., the ECG sensors currently being used for determining the ECG signal are no longer in contact with the patient and need to be switched to other sensors that are in contact with the patient).

As shown in FIG. 4, multiple contacts between the patient and ECG sensor pads are made instantaneously upon application of the patient (e.g., infant/neonate) to a surface of the fabric cover. While the multiple contacts are direct contact points between the skin of the patient and the ECG sensor pads, none of the ECG sensor pads are stuck or mechanically adhered to the patient's skin (e.g., via an adhesive), thereby reducing damage and irritation to the infant/neonate's delicate skin. As also seen in the different views of FIG. 4, the patient is free to move over the surface of the fabric cover and sensor array. As such, the position of the patient on the sensor array may change, and thus which electrodes are in contact with the patient's skin may also change during operation/data collection. As discussed above and further below, the measurement and driven electrodes of the sensory array may be selected and switched according to this movement and change in the contacting sensors.

FIG. 5 shows a flow chart of a method 500 for dynamically switching a driven electrode of a sensor array of an apparatus in direct contact with a patient and determining an ECG signal and/or heart rate of the patient from signals acquired from a plurality of measurement electrodes of the sensor array. In one example, the apparatus may be apparatus 110 shown in FIGS. 1 and 2 and/or may be a fabric cover such as one or more of fabric covers disclosed herein with reference to FIGS. 1, 4, and 6-11. For example, the fabric cover may include one or more aspects of the fabric covers shown in FIGS. 1, 4, and 6-11. As disclosed herein, the apparatus or fabric cover may include a sensor array with a plurality of sensors (e.g., electrodes) spaced apart from one another across a surface of the fabric cover. The fabric cover, and the sensor array, is adapted to be in direct contact with a skin of a patient (e.g., a neonate or infant may be placed directly on top of the sensor array of the fabric cover). However, the patient may freely move across the surface of the fabric cover, thereby changing their position on the cover. As a result, not all sensors of the sensor array may be contacting (via direct contact) the patient at any one time, and which sensors are in contact with the patient may change as the patient moves/changes positions on the cover. As used herein, a "contacting sensor" of the sensor array may be defined as a sensor that is determined to be in direct contact with the skin of the patient and is thereby able to acquire a signal (e.g., bio-potential) from the patient. Additionally, as used herein, "direct contact" refers the electrode contacting the skin of the patient without an intervening components arranged therebetween. In this way, the electrode and the skin of the patient may have face-sharing contact.

Method 500 begins at 502 by, upon placement of a patient (e.g., infant or neonate) in contact with the sensor array of the fabric cover, receiving signals from the plurality of sensors (e.g., electrodes) of the sensor array. As an example, the method at 502 may include receiving (or acquiring) a signal from each sensor included in the sensor array. The received signals may be measurable bio-potentials of the patient and may be of varying strengths (e.g., magnitudes). In some embodiments, if one or more of the sensors are not in direct contact with the patient (e.g., not contacting the patient at all), the received signal maybe be zero, or below a lower threshold level, or measured impedance may be higher than a threshold level. As soon as the patient is placed in contact with the sensor array, signals from the sensors may be automatically and instantaneously acquired by a signal processing circuit of or in electrical communication with the fabric cover.

At 504, the method includes determining which sensors of the sensor array are in direct contact with the patient based on individual skin impedance measurements. For example, the signals received from the sensors at 502 may be used to determine an individual skin impedance measurement corresponding to each sensor. The method at 504 then includes determining, for each sensor of the sensor array, that the individual sensor is in direct contact with the patient (and thus is a contacting sensor) in response to the individual skin impedance measurement of that sensor being above a threshold level. In one example, the threshold level may be a non-zero impedance value indicating that the sensor (which may be a sensor pad, as discussed herein) has a large enough portion of its entire surface area in contact with the skin of the patient in order to obtain a measurable bio-potential signal for determining the ECG signal (and heart rate) of the patient. If the individual skin impedance measurement of a sensor is not below a threshold level, the method at 504 may include determining that the sensor is not in contact with the patient (and thus any signal received from that contact should not be used to determine the ECG signal of the patient).

At 506, the method includes selecting a sensor, out of all the sensors of the sensor array, to be used as a driven electrode based on which sensors are determined to be contacting sensors (e.g., in contact with the patient, as determined at 504) and outputting a driven common mode output signal via the selected sensor. As one example, the driven common mode output signal may be a voltage of a magnitude that is applied continuously via the selected driven sensor to the patient in order to cancel out electromagnetic interference due to patient movement/motion and other environmental artifacts such as power line frequencies etc. As explained above, in one embodiment, all sensors of the sensor array may be measurement sensors adapted to receive and measure bio-potential signals from the patient for processing into the ECG signal of the patient. Each of these measurement sensors may be individually switchable to functioning as the driven electrode by outputting the driven common mode output signal. Any of these measurement sensors may be selected as the driven electrode, if they are determined to be in direct contact with the patient at 504. In another embodiment, the sensor array may be split into a first set of sensors which are measurement sensors which may also be used as the driven electrode and a second set of sensor which are dedicated, driven electrodes. The dedicated, driven electrodes may only be used to deliver the common mode output signal and may not be used to acquire signals from the patient for determining the patient's ECG signal. In one example, the number of dedicated, driven electrodes (sensors) may be less than the number of measurement sensors. In this embodiment, the common mode output signal may be delivered to driven electrode(s) for delivering the common mode output signal to the patient. If more than one dedicated, driven sensor is in contact with the patient, the sensor outputting the highest skin impedance measurement may be selected to be the driven electrode. Alternatively, if more than one dedicated, driven sensor is in contact with the patient, the processor may randomly select one of the contacting, dedicated, driven sensors to be the driven electrode. In yet another example, if more than one dedicated, driven sensor is in contact with the patient, the processor may select a pre-determined (e.g., stored in a memory of the signal processing circuit) to be the driven electrode and output the driven common mode output signal. In yet another example, if more than one dedicated, driven sensor is in contact with the patient, the processor may select all the dedicated driven electrodes and output the driven common mode output signal. If none of the dedicated, driven sensors are in direct contact with the patient, the processor may then select one of the measurement sensors that is in direct contact with the patient to be the driven electrode and switch the selected measurement electrode from measuring bio-potentials of the patient to outputting the driven common mode output signal. Examples of selecting the sensor to be used as the driven electrode based on position of the patient are shown in FIG. 4, as discussed above.

Method 500 then continues to 508 to receive (or continue receiving) signals from the contacting measurement sensors (e.g., measurement sensors in contact with the patient). In one example, only the measurement sensors in direct contact with the patient may acquire signals from the patient and transfer these to the signal processing circuit. In another example, signals may be received by the signal processing circuit from every individual measurement sensor, even if the sensor is not in contact with the patient, and then only the received signals from sensors with low contact impedance below a threshold may be used to determine the ECG signal, as described further below.

At 510, the method includes filtering the signals received from the measurement sensors. As described above with reference to FIG. 3, the filters may include one or more filters of varying types such as adaptive filters, band-pass filters, and the like. The method then continues to 512 to use the filtered signals from the measurement sensors determined to be contacting (e.g., in direct contact with) the patient to determine the ECG signal for the patient and determine a heart rate of the patient from the determined ECG signal. For example, the dynamic switching circuit of the signal processing circuit may be adapted to select the filtered signals from only the measurement sensors determined to be in direct contact with the patient (e.g., via an input switch matrix, such as the input switch matrix 308 shown in FIG. 3) and then determine the patient's ECG signal from only these selected filtered signals. The patient's heart rate may then be determined directly from the determined ECG signal.

At 514, the method includes outputting the ECG signal and/or the heart rate to a user via an output device. In one example, the output device may be a display device in electronic communication with the signal processing circuit. The user may be a medical provider, such as a technician, physician, or nurse. Method 500 may be run continuously such that the ECG signal and/or heart rate are continually determined and updated and the display device may continuously display the updated signals, while signals are acquired from the patient via the sensor array of the fabric cover. In this way, the user may monitor a condition of the patient while the patient is in contact with the fabric cover, with minimal intervention (e.g., no adhesive electrodes are stuck to the patient's skin).

Continuing to 516, the method includes determining whether the contacting sensors have changed. For example, the method at 516 may include determining whether the sensor previously (or most recently) selected as the driven electrode is no longer contacting the patient. In this case, the currently selected driven sensor may not be able to deliver the driven common mode output signal for noise reduction. If the contacting sensors have not changed, the method continues to 518 to continue acquiring signals from the measurement sensors and using the same (previously selected) sensor as the driven sensor. If any of the contacting measurement sensors have changed, the method may further include continuing to acquire signals from the measurement sensors but switching which measurement sensors signals are used to determine the ECG signal (e.g., via selecting the signals from only the sensors directly contacting the patient).

If the contacting sensors have changed, the method continues to 520 to dynamically switch which sensor is used as the driven sensors (e.g., electrode) while continuing to acquire signals from the contacting measurement sensors, if the currently-selected driven sensor is no longer contacting the patient. For example, the method at 520 may include switching from outputting the driven common mode output signal from a first sensor (determined to be no longer in direct contact with the patient) to outputting the driven common mode output signal from a second sensor (determined to be in direct contact with the patient). An example of such switching of which sensor is used as the driven electrode is shown in FIG. 4, as described above. Dynamically switching which sensor is used as the driven electrode may include switching, in real-time, as signals are continually acquired from the measurement sensors and as the patient moves across a surface of the sensor array (and changes position), which sensor outputs the driven common mode output signal. The switching at 520 may also include, if one or more measurement sensors are no longer contacting the patient, switching which measurement sensors are used to determine the ECG signal.

FIGS. 6-10 show example arrangements of electrodes for a fabric cover, such as one of the fabric covers discussed herein. In particular, the fabric cover may be similar to the apparatus 110 and/or fabric covers 106 and 410 described above with reference to FIGS. 1-4. Thus, the fabric covers discussed below with reference to FIGS. 6-10 may include similar components, including a sensor array including a plurality of sensors integrated with a remainder of the fabric cover. In some embodiments, the fabric cover may be a bed sheet, mattress cover, blanket, or wearable article such as a sling or wrap. The plurality of sensors may be in the form of electrode pads and may be adapted to be measurement and/or driven electrodes, as discussed herein. In one embodiment, both the fabric base of the fabric cover and the electrode pads may be porous in order to interface with the skin and allow for the exchange of humidity and gases through them, while still enabling measurement from the electrode pads. The array of electrode pads on a surface of the fabric cover may be sized to include a selected number of electrode pads to accommodate a range of sizes of patients from neonates to older babies to adults.

The fabric covers discussed below with reference to FIGS. 6-10 may be optimized to maximize a separation distance (e.g., gap) between adjacently arranged electrodes (e.g., electrode pads), maximize a number of the electrodes within the electrode array, maximize the electrodes separation distance, and maximize a surface area of each electrode. For example, by having an increased number of potential contact points (where each electrode pad is considered a contact point) while at the same time maximizing a surface are of each contact point, within a set area for the electrode array (referred to as the measurement area, as explained further below), an increased number of sensor signals for determining the ECG signal may be acquired, even as the patient changes position on the fabric cover, thereby increasing an accuracy of the ECG signal and reducing signal noise. Maximizing the separation distance between electrodes allows acquisition of a stronger signal peak-peak voltage. The various embodiments discussed below with reference to FIGS. 6-10 aim to achieve this arrangement of electrode pads.

Figure 6:
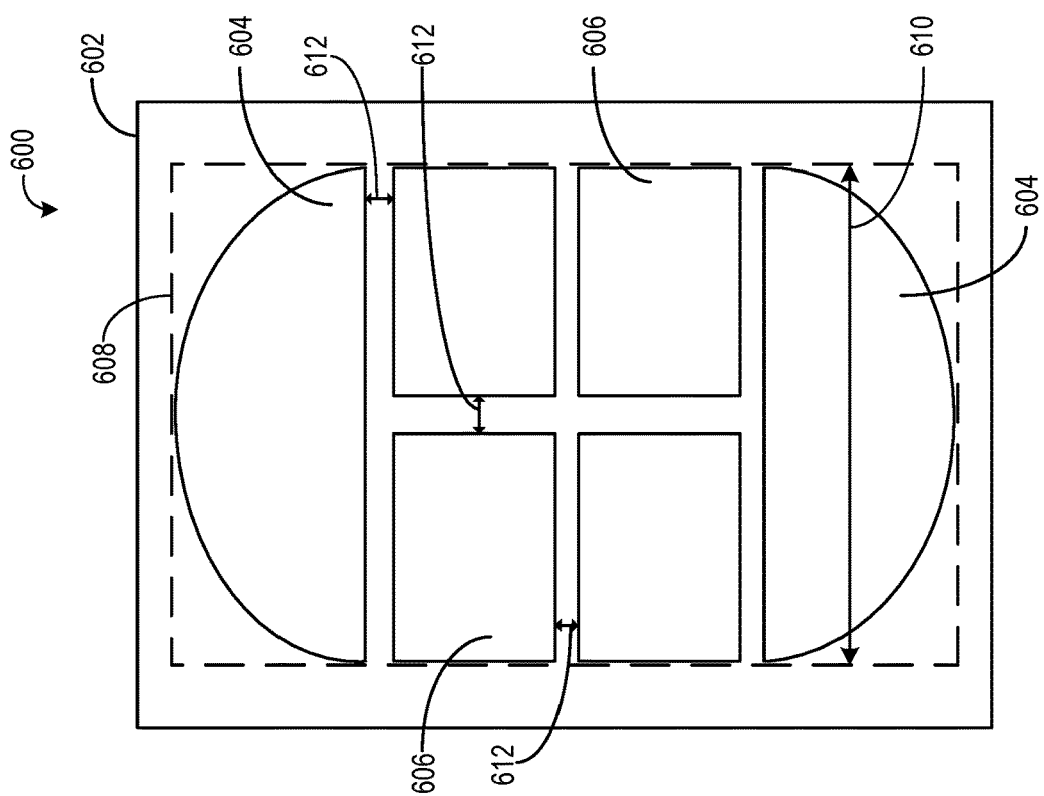

Turning first to FIG. 6, a first embodiment of a fabric cover 600 is shown having a fabric base 602 with a plurality of electrode pads integrated therein. The electrode pads include semi-circular electrode pads 604 arranged at topmost and bottommost positions of a measurement area 608 of the fabric base 603 of fabric cover 600 while a plurality of rectangular electrode pads 606 are arranged therebetween. In alternate embodiments, electrode pads 606 may have a different shape, such as square, circular, semi-circular, oval, hexagonal, or the like.

The measurement area 608 is defined as the area of the fabric cover including all the electrode pads of the sensor array of the fabric cover. There may be no electrode pads (e.g., electrodes) arranged outside a perimeter of the measurement area 608. As shown in FIG. 6, both the semi-circular electrode pads 604 extend across an entire width 610 of the measurement area 608 and each of the rectangular electrode pads extend across only a portion of the width 610. By having topmost and bottommost electrode pads that extend across an entire width of the measurement area, it may be more likely to obtain a contact point at either end of the patient. For example, both of the semi-circular electrode pads 604 may be dedicated driven electrodes, and the extent and shape of the semi-circular electrode pads may optimize contact with the patient's head if the patient is rolling or moving relative to the fabric cover.

Each electrode pad of the rectangular electrode pads 606 is arranged directly adjacent to two other electrode pads of the rectangular electrode pads 606 and one of the semi-circular electrode pads 604. The spacing, arrangement, and/or shape of the rectangular electrode pads 606 may optimize contact with the torso area of the patient for ECG signal acquisition. There is a gap 612 arranged between adjacently arranged electrode pads. The gap 612 may be of varying sizes. In one example, gap 612 may be less than a threshold distance, such as half an inch. However, in alternate examples, gap 612 may be between 0.25 and 0.5 inches or between 0.4 and 0.6 inches. The larger the gap between two signal electrodes, the higher the skin impedance is between them, and therefore the larger the amplitude of the measured ECG signal is. The material within gaps 612, between the electrode pads, is the fabric material of the fabric base 602 and may be insulating such that electrical signals are not transferred between adjacent electrode pads.

Figure 7:
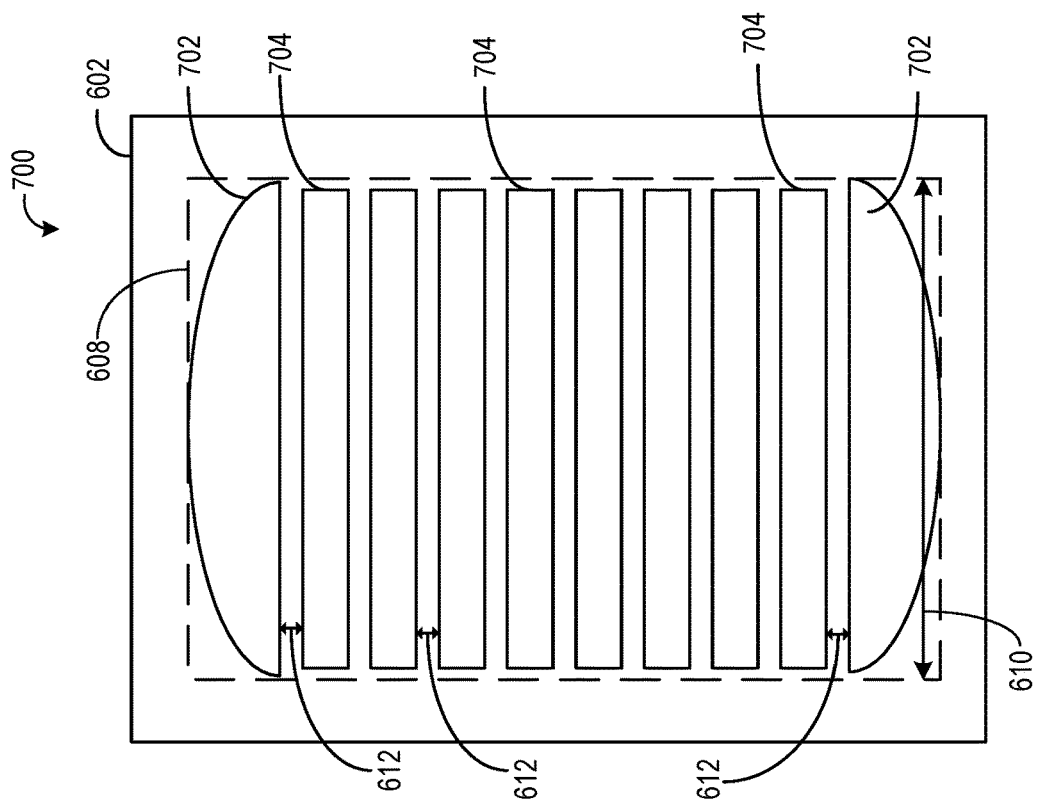
FIGS. 6-10 show example arrangements of electrodes for a fabric cover adapted to be placed in direct contact with a patient.

FIG. 7 shows a second embodiment of a fabric cover 700 having the fabric base 602 with a plurality of electrode pads integrated therein. In this embodiment, the electrode pads include semi-circular electrode pads 702 arranged at topmost and bottommost positions of measurement area 608. Semi-circular electrode pads 702 have a smaller height (direction perpendicular to width 610) than the semi-circular electrode pads 604 of FIG. 6. The electrode pads also include rectangular electrode pads 704 which each extend across a majority of the entire width 610 of measurement area 608. In alternate embodiment, each of or a portion of electrode pads 704 may extend across the entire width 610. Further, in some embodiments, rectangular electrode pads 704 may have an alternate shape such as oval, rectangular with semi-circular ends, semi-circular, or the like. As in FIG. 6, adjacent electrode pads are separated by gap 612 which may vary between different pairs of electrode pads or may be the same for each adjacent pair of electrode pads.

The fabric covers disclosed herein may be comprised of a fabric material, including one or more of cotton, nylon, rayon, spandex, or the like. The electrodes (electrode pads) and electrical connections between the electrode pads and connectors or connecting elements, as well as the connectors (or leads) may be comprised of a conductive deposited material such as silver. For example, the electrode pads and electrical connections and/or connectors may be silver deposited electrode layers on a fabric base comprising one or more of the fabric materials listed above. A masking or etching process may be used to define the active electrode areas and their corresponding conductive electrical connections (e.g., signal routes to the connectors). This is in contrast to the non-conductive or insulated areas of the fabric base of the fabric cover. Using silver material for the electrodes and/or signal paths may allow for electrical signal transmission, while at the same time providing antibacterial properties with increased bio-compatibility. Signal routing paths (electrical connections) from each electrode pad to a connector or measurement point at an electronic interface of the fabric cover may be insulated from undesired patient skin contact by the addition of a dielectric layer. The electrical contacts or connectors (such as connector 210 shown in FIG. 2) measuring or receiving the signals from each electrode pad may be a simple connector with spring force contact pads on the fabric base with sufficient pitch density, thereby enabling the connection to pass bio-potential signals to a data acquisition front end device (e.g., which may be part of the signal processing unit), either via a wired cable from the connector, or directly to an integrated electronic layer performing measurements on the fabric cover and transmitting the data to a monitoring station wirelessly.

The fabric cover may be intended for single use or repeated use. For example, the fabric cover may be washable between uses (e.g., between patients). However, the fabric cover may have a finite number of uses as the electrical contacts and/or electrode pads may degrade over time due to contact with water during washing.

Figure 9:
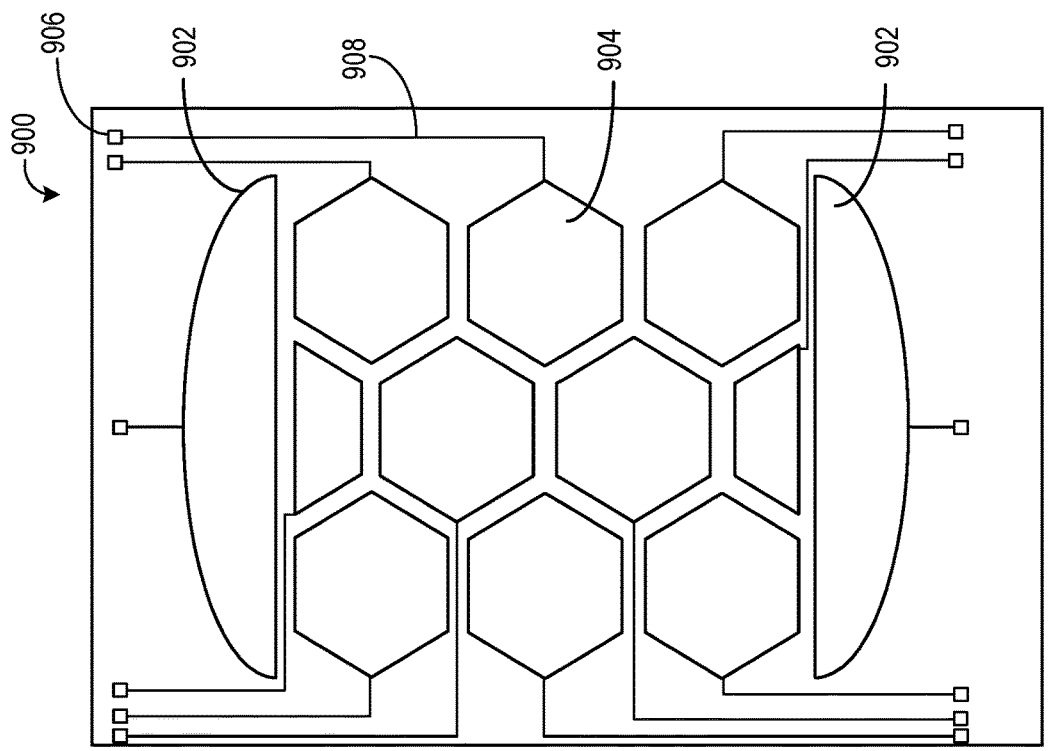
Figure 8:
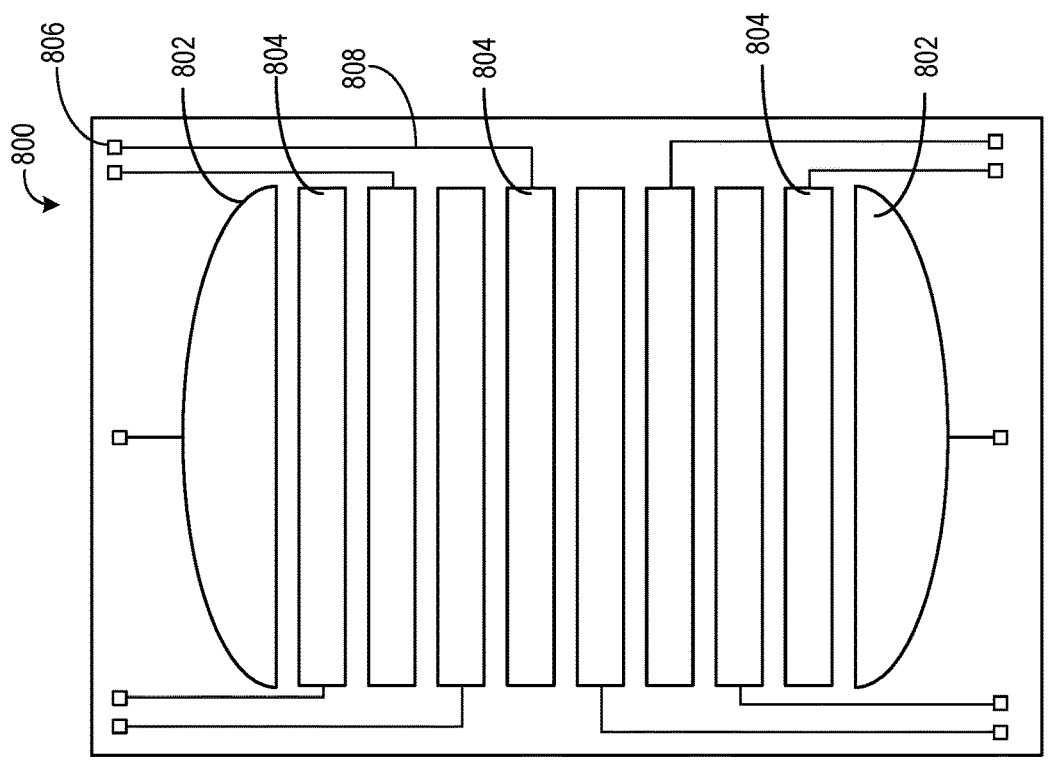
Figure 10:
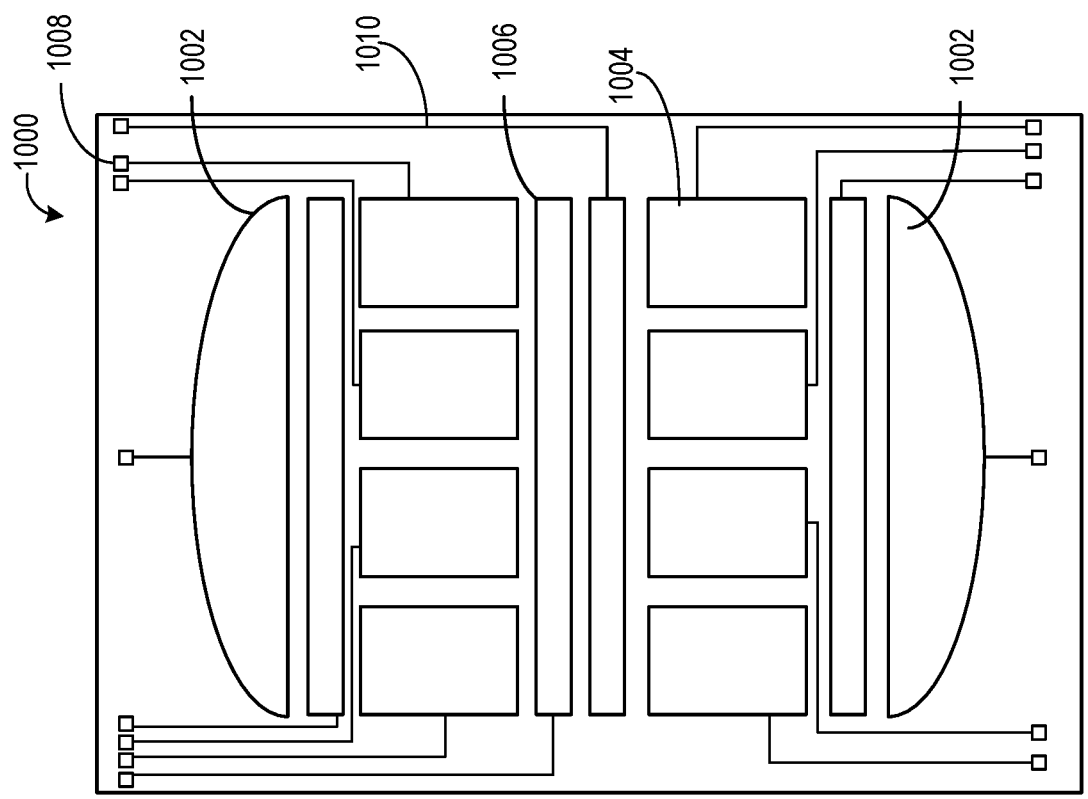

Turning now to FIGS. 8-10, additional embodiments of arrangements of electrode pads of a fabric cover and electrical connections (e.g., signal routes) from each electrode pad to a measurement point (which may include a connector, in one example) are shown. In particular, FIG. 8 shows a first fabric cover 800 with a similar arrangement of electrode pads to that of FIG. 7. For example, fabric cover 800 includes topmost and bottommost semi-circular electrode pads 802 and a plurality of elongate electrode pads 804 arranged therebetween. Each electrode pad is coupled to an individual measurement point 806 by an electrical connection 808. Each measurement point 806 may be coupled to or include its own connector (e.g., similar to connector 210 of FIG. 2) or all measurement points on a same side of the fabric cover may couple to a common connector, the common connector in electronic communication with additional signal processing electronics via a wired or wireless connection. All or a portion of the additional signal processing electronics may be included on the fabric cover or off (e.g., remote from) the fabric cover.

FIG. 9 shows a second fabric cover 900 with a different arrangement of electrode pads including topmost and bottommost semi-circular electrode pads 902 and a plurality of hexagonal electrode pads 904 arranged between. Some of the hexagonal electrode pads 904 may be partial (e.g., cut in half) hexagons in order to accommodate a honey-comb like arrangement of the hexagonal electrode pads (e.g., adjacent hexagons are offset in an alternating pattern), as shown in FIG. 9. Each of the hexagonal electrode pads 904 are spaced apart from one another and the semi-circular electrode pads 904. In alternate embodiments, the hexagonal electrode pads 904 may have an alternate polygon shape, such as pentagonal, heptagonal, octagonal, decagonal, and the like. Similarly to as described above with reference to FIG. 8, each electrode pad of FIG. 9 is coupled to an individual measurement point 906 by an electrical connection 908.

FIG. 10 shows a third fabric cover 1000 with yet another arrangement of electrode pads including topmost and bottommost semi-circular electrode pads 1002, a plurality of elongate electrode pads 1006, and a plurality of rectangular electrode pads 1004. Specifically, FIG. 10 shows two rows of rectangular electrode pads 1004 separated from one another via two elongate electrode pads 1006 (which are spaced apart from one another and an adjacently arranged row of rectangular electrode pads 1004), and an elongate electrode pad 1006 positioned between each row of rectangular electrode pads 1004 and one of the semi-circular electrode pads 1002. However, in alternate embodiments, the third fabric cover 1000 may include additional or fewer rows of rectangular electrode pads 1004 and more or fewer elongate electrode pads 1006 spaced between adjacent rows of rectangular electrode pads 1004 and/or a row of rectangular electrode pads 1004 and a semi-circular electrode pad 1002. Similarly to as described above with reference to FIG. 8, each electrode pad of FIG. 10 is coupled to an individual measurement point 1008 by an electrical connection 1010.

FIG. 11 shows a schematic view 1100 of a patient 1124 positioned on a care provider 1102 and held in position with a fabric cover 1110. Fabric cover 1110 may be similar to apparatus 110 and/or fabric cover 106 discussed above with reference to FIGS. 1-3. However, as shown in FIG. 11, the fabric cover 1110 may be in the form of a wearable article configured to facilitate skin-to-skin contact between the patient 1124 and the care provider 1102 (which may be a parent of the patient or other care provider). Thus, the fabric cover 1110 may be in the form of a wrap, a sling, a carrier, a nursing top, or other wearable article. As shown, the patient 1124 is positioned between the care provider 1102 and the fabric cover 1110, such that the patient 1124 is in direct, skin-to-skin contact with the care provider 1102 (e.g., via a first side of the patient) and the patient 1124 is in direct, skin-to-fabric and/or electrode contact with the fabric cover 1110 (e.g., via a second, opposite side of the patient).

As discussed above, the fabric cover 1110 includes a plurality of integrated ECG sensors 1112, 1114, 1116, 1118, 1120, and 1122 which may be referred to herein as electrodes or electrode pads. Each of the ECG sensors are spaced apart from one another such that they are electrically insulated from one another (and thus cannot pass signals between one another, thereby reducing signal interference between ECG sensors) via the intervening fabric of the fabric cover 1110. FIG. 11 shows an example arrangement of ECG sensors on the fabric cover 1110 which is not meant to be limiting and other arrangements of ECG sensors are possible. Further, the ECG sensors on the fabric cover 1110 may be positioned on a patient-facing surface of the fabric cover 1110, such that the electrodes may make direct contact with the patient 1124, while an insulating layer (not shown in FIG. 11 for visual purposes) may form an outer-facing surface of the fabric cover 1110.

As shown in the example of FIG. 11, the ECG sensors include a topmost ECG sensor 1112, a top-left ECG sensor 1114, a bottom-left ECG sensor 1116, a bottommost ECG sensor 1118, a bottom-right ECG sensor 1122, and a top-right ECG sensor 1120. The patient 1124 may be smaller than the fabric cover 1110 and thus may move around across the patient-facing surface of the fabric cover 1110. As such, at different points in time, the skin of the patient may be in contact with different ECG sensors of fabric cover 1110. Thus, the dynamic switching circuit of the signal processing circuit included in or electrically coupled with the fabric cover 1110 (such as dynamic switching circuit 300 of FIG. 3) may switch, in real-time (e.g., dynamically), which ECG sensors are selected as the measurement electrodes and driven electrode for producing the patient's ECG signal and determining the patient's heart rate, based on the patient's position on the fabric cover 1110 (as determined according to the methods described herein with reference to FIG. 3 and FIG. 5).

The fabric cover 1110 may be similar to the fabric covers described above, and thus may be comprised of a fabric material, including one or more of cotton, nylon, rayon, spandex, or the like. The electrodes may be similar to the electrodes described above, and thus the electrodes (electrode pads) and electrical connections between the electrode pads and connectors or connecting elements, as well as the connectors (or leads) may be comprised of a conductive deposited material such as silver, e.g., silver deposited electrode layers on a fabric base comprising one or more of the fabric materials listed above.

The fabric cover 1110 may be configured to maximize electrode contact with the patient 1124 while minimizing electrode contact with the care provider 1102. Thus, the electrodes integrated in the fabric cover 1110 may be positioned on the fabric cover 1110 in a measurement region that is positioned to preferentially contact the patient. The fabric cover may include straps, fasteners, or other features not shown in FIG. 11 to facilitate secure positioning of the patient 1124 relative to the care provider 1102 while also ensuring maximum contact between the patient 1124 and the electrodes. The fabric cover 1110 may include an insulating layer on an outer-facing surface of the fabric cover 1110, opposite the patient-facing surface and integrated electrodes, which may prevent contact between the care provider 1102 and the electrodes.

However, given the high likelihood for patient movement and small size of the patient relative to the care provider 1102, and further given the desire to maximize patient contact with the electrodes even as the patient moves (and hence wide/long extension of the electrodes across the fabric cover), it may not be possible to prevent inadvertent contact between one or more of the electrodes and the care provider during all conditions, or otherwise insulate the care provider from contributing interference to the ECG signal of the patient. Thus, at least in some examples, before and/or during patient ECG signal acquisition, a diagnostic routine may be performed to determine if the care provider is contributing to the ECG signal acquired by the system. If the care provider is contributing to the ECG signal, the acquisition of the ECG signal may be paused until the care provider is no longer contributing to the ECG signal, or the contribution to the ECG signal from the care provider may be filtered out.

FIGS. 1 and 6-10 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

In this way, a fabric cover may include a plurality of electrodes arranged on a surface of the fabric cover in order to measure and ECG signal and/or a heart rate of a patient. The surface of the fabric cover is adapted to have direct contact with the patient (e.g., the patient may be placed on top of and/or against the fabric cover). However, the electrodes may not be mechanically adhered (via adhesive or other means) to the patient and the patient may be allowed to feely move across the surface of the fabric cover. As such, a signal processing circuit of the fabric cover may determine which electrodes of the plurality of electrodes have direct contact with the patient's skin and, during signal acquisition via the electrodes, dynamically switch which electrode of the plurality of electrodes is used to output a driven, common mode output signal and which electrode signals are used to determine the patient's ECG signal. As a result, a more accurate ECG signal and heart rate of the patient, with reduced noise, may be acquired and used for diagnosis and interventions, even as the patient moves across and changes position on the fabric cover. The technical effect of, while a patient is in direct contact with a fabric surface having a plurality of electrodes integrated therein, receiving signals from the plurality of electrodes; selecting at least a first electrode of the plurality of electrodes as a measurement electrode and a second electrode of the plurality of electrodes as a driven electrode based on the received signals; receiving and processing signals from at least the first electrode to determine and output an electrocardiogram signal of the patient with reduced noise; and dynamically switching which electrode of the plurality of electrodes is selected as the driven electrode in response to a change in which electrodes of the plurality of electrodes are in direct contact with the patient is to obtain, more quickly, a more accurate ECG signal and heart rate with reduced noise, while also reducing irritation to the patient's skin. As such, in situations where time to intervene or treat a patient is more critical (as for an infant or neonate following delivery), patient treatment based on ECG signal and/or heart rate may be delivered more quickly and effectively.

As one embodiment, a fabric cover for an infant incubator or warmer includes a plurality of electrodes spaced apart from one another within a measurement area of a surface of the fabric cover adapted to have direct contact with a patient, the plurality of electrodes including a topmost electrode extending across an entire width of the measurement area, a bottommost electrode extending across the entire width of the measurement area, and a set of electrodes arranged between the topmost electrode and bottommost electrode, in a direction perpendicular to the width, within the measurement area. In a first example of the fabric cover, each electrode of the set of electrodes extends across a majority of the entire width of the measurement area. In a second example of the fabric cover, which optionally includes the first example, each electrode of the set of electrodes is arranged directly adjacent to two other electrodes of the set of electrodes and one of the topmost and bottommost electrodes. In a third example of the fabric cover, which optionally includes one or both of the first and second examples, the topmost electrode and the bottommost electrode are dedicated, driven electrodes and wherein each electrode of the set of electrodes is a measurement electrode. In a fourth example of the fabric cover, which optionally includes one or more or each of the first through third examples, each electrode of the plurality of electrodes and the fabric cover are porous. In a fifth example of the fabric cover, which optionally includes one or more or each of the first through fourth examples, the fabric cover further includes at least one electrical connector and a plurality of electrical leads, each electrical lead of the plurality of electrical leads being insulated from the plurality of electrodes via a dielectric layer and extending between a respective electrode and the at least one electrical connector. In a sixth example of the fabric cover, which optionally includes one or more or each of the first through fifth examples, the at least one electrical connector is wirelessly connected to a signal processing circuit via a wireless electrical connection. In a seventh example of the fabric cover, which optionally includes one or more or each of the first through sixth examples, the fabric cover further includes an integrated electronic layer electrically coupled to the at least one electrical connector and adapted to perform measurements on electrical signals received from the plurality of sensors. In an eighth example of the fabric cover, which optionally includes one or more or each of the first through seventh examples, the integrated electronic layer includes a dynamic switching circuit including an input switch matrix and output switch matrix adapted to switch which electrode of the plurality of electrodes is driven to output a driven common mode output signal and which signals received from the plurality of electrodes are used to determine an electrocardiogram signal of the patient. In a ninth example of the fabric cover, which optionally includes one or more or each of the first through eighth examples, the plurality of electrodes receive electrical power via a battery incorporated into the fabric cover. In a tenth example of the fabric cover, which optionally includes one or more or each of the first through ninth examples, each electrode of the plurality of electrodes is an electrode pad including silver deposited electrode layers and wherein each electrode and a corresponding electrical connection between the electrode and an electrical connector or measurement electronics is conductive while a remainder of the fabric cover is non-conductive.

As another embodiment, a system for measuring biopotentials of a patient includes a plurality of electrodes spaced apart from one another along a surface adapted to be placed in direct contact with the patient; and an electronic processor in electronic communication with each of the plurality of electrodes and adapted to: obtain signals output from at least two measurement electrodes of the plurality of electrodes that are in direct contact with the patient and dynamically switch which electrode of the plurality of electrodes is selected as a driven electrode while at least a portion of the surface is in contact with the patient. In a first example of the system, the plurality of electrodes includes a first set of dedicated, driven electrodes adapted to only output a driven common mode output signal and second set of measurement electrodes adapted to measure bio-potentials of the patient, where the driven electrode is selected from the first set of dedicated, driven electrodes and the two measurement electrodes are selected from the second set of measurement electrodes. In a second example of the system, which optionally includes the first example, the first set of dedicated, driven electrodes includes at least two electrodes, wherein there are a greater number of electrodes in the second set of measurement electrodes than the first set of dedicated, driven electrodes, and wherein the plurality of electrodes are spaced apart from one another via a gap, that gap including material that insulates adjacent electrodes from one another. In a third example of the system, which optionally includes one or both of the first and second examples, the electronic processor is further adapted to: determine which electrodes of the plurality of electrodes are in direct contact with the patient based on individual skin impedance measurements received from each electrode of the plurality of electrodes and select the driven electrode to be an electrode having an individual skin impedance measurement at a threshold level. In a fourth example of the system, which optionally includes one or more or each of the first through third examples, the electronic processor is further adapted to determine an electrocardiogram signal of the patient from signals output by the at least two measurement electrodes, the at least two measurement electrodes determined to be in direct contact with the patient, wherein the electrodes having signals used for determining the electrocardiogram signal do not include the selected driven electrode. In a fifth example of the system, which optionally includes one or more or each of the first through fourth examples, the electronic processor is further adapted to determine a heart rate of the patient from the determined electrocardiogram signal and display, via a display device, one or more of the determined heart rate and electrocardiogram signal.

As yet another embodiment, a method includes, while a patient is in direct contact with a fabric surface having a plurality of electrodes integrated therein: receiving signals from the plurality of electrodes; selecting at least a first electrode of the plurality of electrodes as a measurement electrode and a second electrode of the plurality of electrodes as a driven electrode based on the received signals; receiving and processing signals from at least the first electrode to determine and output an electrocardiogram signal of the patient with reduced noise; and dynamically switching which electrode of the plurality of electrodes is selected as the driven electrode in response to a change in which electrodes of the plurality of electrodes are in direct contact with the patient. In a first example of the method, the dynamically switching includes receiving a signal that the second electrode is no longer in direct contact with the patient and selecting a different, third electrode out of the plurality of electrodes as the driven electrode and switching to delivering a driven common mode output signal to the patient from the first electrode to the third electrode while continuing to determine and output the electrocardiogram signal. In a second example of the method, which optionally includes the first example, selecting at least the first electrode of the plurality of electrodes as a measurement electrode includes receiving signals from the plurality of electrodes, determining which signals indicate a corresponding electrode of the plurality of electrodes is in direct contact with the patient, and processing signals of each corresponding electrode indicated as being in direct contact with the patient to determine the electrocardiogram signal and further comprising displaying one or more of the determined electrocardiogram signal and a heart rate determined from the electrocardiogram signal via a display device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   while a patient is in direct contact with a surface of a fabric cover having a plurality of electrodes integrated therein:
   receiving signals from the plurality of electrodes;
   selecting at least a first electrode of the plurality of electrodes as a measurement electrode and a second electrode of the plurality of electrodes as a driven electrode based on the received signals;
   receiving and processing signals from at least the first electrode to determine and output an electrocardiogram signal of the patient;
   determining which electrodes of the plurality of electrodes are in direct contact with the patient; and
   dynamically switching which electrode of the plurality of electrodes is selected as the driven electrode in response to a change in which electrodes of the plurality of electrodes are in direct contact with the patient and a position of the patient on the surface of the fabric cover.

2. The method of claim 1, wherein the dynamically switching includes receiving a signal that the second electrode is no longer in direct contact with the patient and selecting a different, third electrode out of the plurality of electrodes as the driven electrode and switching to delivering a driven common mode output signal to the patient from the first electrode to the third electrode while continuing to determine and output the electrocardiogram signal.

3. The method of claim 2, wherein selecting at least the first electrode of the plurality of electrodes as a measurement electrode includes receiving signals from the plurality of electrodes, determining which signals indicate a corresponding electrode of the plurality of electrodes is in direct contact with the patient, and processing signals of each corresponding electrode indicated as being in direct contact with the patient to determine the electrocardiogram signal.

4. The method of claim 1, further comprising displaying one or more of the determined electrocardiogram signal and a heart rate determined from the electrocardiogram signal via a display device.

5. The method of claim 1, wherein dynamically switching which electrode of the plurality of electrodes is selected as the driven electrode comprises dynamically switching, in real-time, which electrode of the plurality of electrodes is selected as the driven electrode as signals are continually acquired from the measurement electrode and as the patient moves across the surface of the fabric cover.

6. A method, comprising:
designating a first electrode from a plurality of electrodes integrated in a fabric cover to be a driven electrode and designating a first subset of electrodes from the plurality of electrodes to be measurement electrodes;
outputting a driven common mode output signal via the first electrode;
outputting an electrocardiogram (ECG) signal of a patient based on signals received from the first subset of electrodes; and
changing which electrodes from the plurality of electrodes are designated as the driven electrode and/or the measurement electrodes based on a position of the patient on a surface of the fabric cover.

7. The method of claim 6, wherein the changing includes designating a second electrode from the plurality of electrodes to be the driven electrode and outputting the driven common mode output signal via the second electrode.

8. The method of claim 7, wherein the first subset of electrodes includes the second electrode and the changing includes switching the second electrode from being a measurement electrode to being the driven electrode.

9. The method of claim 6, wherein the changing includes designating a second subset of electrodes from the plurality of electrodes to be the measurement electrodes and outputting the ECG signal of the patient based on signals received from the second subset of electrodes.

10. The method of claim 6, further comprising designating one or more remaining electrodes of the plurality of electrodes to be non-contacting sensors and wherein signals from the one or more remaining electrodes are not used to output the ECG signal.

11. The method of claim 10, wherein the changing includes changing which electrodes from the plurality of electrodes are designated as the non-contacting sensors based on the position of the patient on the surface of the fabric cover.

12. A method, comprising:
identifying a plurality of contact electrodes of an electrode array, wherein the plurality of contact electrodes is determined to be in direct contact with a patient based on individual skin impedance measurements and wherein the electrode array is integrated in a fabric cover;
selecting one contact electrode from the plurality of contact electrodes to be a driven electrode and designating remaining electrodes from the plurality of contact electrodes to be measurement electrodes;
outputting a driven common mode output signal via the driven electrode;
receiving signals from the electrode array;
filtering the signals from the electrode array;
selecting the filtered signals from only the measurement electrodes and determining an electrocardiogram (ECG) signal of the patient from only the selected filtered signals;
displaying one or more of the determined ECG signal and a heart rate determined from the ECG signal via a display device; and
changing which electrodes of the electrode array are identified as the driven electrode and/or the measurement electrodes based on a position of the patient on a surface of the fabric cover.

13. The method of claim 12, wherein identifying the plurality of contact electrodes comprises identifying that a first electrode, a second electrode, and a third electrode of the electrode array are each in direct contact with the patient, wherein selecting the one contact electrode to the driven electrode comprises selecting the first electrode to be the driven electrode, and wherein the second electrode and the third electrode are designated as the measurement electrodes.

14. The method of claim 13, wherein changing which electrodes of the electrode array are identified as the driven electrode and/or the measurement electrodes based on a position of the patient on a surface of the fabric cover further comprising identifying, based on the position of the patient, that the third electrode is no longer in direct contact with the patient and that a fourth electrode is in direct contact with the patient, and in response, designating the second electrode and the fourth electrode as the measurement electrodes.

15. The method of claim 14, further comprising in response to the identifying that the third electrode is no longer in direct contact with the patient and that the fourth electrode is in direct contact with the patient, adjusting the selecting of the filtered signals so that signals from the third electrode are not selected.

16. The method of claim 12, wherein filtering the signals from the electrode array comprises applying one or more adaptive filters to the signals from the electrode array to filter out common motion noise.

17. The method of claim 12, wherein selecting the filtered signals from only the measurement electrodes comprises selecting the filtered signals form only the measurement electrodes via an input switch matrix configured to determine which electrodes of the electrode array have contact with the patient and select signals received from the measurement electrodes to transfer to an analog-to-digital converter for further processing and determination of the ECG signal and heart rate.

* * * * *